(12) United States Patent
Susilo

(10) Patent No.: US 7,615,238 B2
(45) Date of Patent: Nov. 10, 2009

(54) PLASTER FOR THE TREATMENT OF DYSFUNCTIONS AND DISORDERS OF NAILS, COMPRISING SERTACONAZOLE

(75) Inventor: Rudy Susilo, Köln (DE)

(73) Assignee: Trommsdorff GmbH & Co. KG Arzneimitttel, Alsdorf (DE)

( * ) Notice: Subject to any disclaimer, the term of this patent is extended or adjusted under 35 U.S.C. 154(b) by 439 days.

(21) Appl. No.: 10/488,905

(22) PCT Filed: Sep. 4, 2002

(86) PCT No.: PCT/EP02/09910

§ 371 (c)(1),
(2), (4) Date: Aug. 5, 2004

(87) PCT Pub. No.: WO03/020248

PCT Pub. Date: Mar. 13, 2003

(65) Prior Publication Data

US 2004/0247657 A1    Dec. 9, 2004

(30) Foreign Application Priority Data

Sep. 4, 2001 (EP) .................................. 01121200

(51) Int. Cl.
*A61K 9/70* (2006.01)
(52) U.S. Cl. ...................................... 424/449; 424/400
(58) Field of Classification Search .................. 424/449
See application file for complete search history.

(56) References Cited

U.S. PATENT DOCUMENTS

| | | | | |
|---|---|---|---|---|
| 5,374,633 A | * | 12/1994 | Parab | ......................... 514/171 |
| 5,464,610 A | | 11/1995 | Hayes, Jr. et al. | |
| 5,753,256 A | * | 5/1998 | Cordes et al. | ................ 424/443 |
| 5,993,790 A | * | 11/1999 | Strauss | ......................... 424/61 |
| 2004/0265362 A1 | * | 12/2004 | Susilo | ......................... 424/449 |

FOREIGN PATENT DOCUMENTS

| WO | WO 98/16251 | 4/1998 |
|---|---|---|
| WO | WO 99/40955 | 8/1999 |
| WO | WO 03/020248 | 3/2003 |

OTHER PUBLICATIONS

International Search Report, PCT/EP02/09910, May 12, 2002.

* cited by examiner

*Primary Examiner*—M P Woodward
*Assistant Examiner*—Aradhana Sasan
(74) *Attorney, Agent, or Firm*—Turocy & Watson, LLP

(57) ABSTRACT

The present invention relates to plasters for prophylaxis and/or treatment of a dysfunction or disorder of nails, especially onychomycosis, onychocryptosis, nail psoriasis, melanonychia striata, and onychodystrophy, the use of said plasters and methods for prophylaxis and/or treatment of a dysfunction or disorder of nails using said plasters. Said dysfunction or disorder of nails may be induced or caused by drugs, systemic diseases, chemical compounds, physical influences, fungal, yeast, or bacterial infection of the nails and/or the nail beds, or in the context of skin diseases. The plasters show good therapeutically effects on said dysfunction or disorder of nails without the need of drilling a hole into the nail and/or daily scraping of the nail. Preferred embodiments of the plasters consist of an occlusive backing layer and a layer attached to said backing layer. The layer comes in close contact with the nail and optionally with the surrounding skin. The layer is made of a adhesive, a skin and/or nail permeation enhancer, a therapeutically effective amount of sertaconazole, and suitable additives, and/or further pharmaceutically active agents.

52 Claims, No Drawings

PLASTER FOR THE TREATMENT OF DYSFUNCTIONS AND DISORDERS OF NAILS, COMPRISING SERTACONAZOLE

The present invention relates to plasters for prophylaxis and/or treatment of onychomycosis or dysfunctions or disorders of nails, the use of said plasters and methods for prophylaxis and/or treatment of onychomycosis or dysfunctions or disorders of nails or in combination with systemic antimycotics using said plasters.

BACKGROUND OF THE INVENTION

Dysfunction and disorder of nails caused by e.g. onychomycosis is an increasingly common and recalcitrant fungal nail infection world-wide.

A dysfunction or disorder of nails is often induced or caused by fungal infections of the nails and/or nail beds. Particularly in the later stages of such an infection said dysfunctions or disorders are difficult to treat. Said dysfunctions or disorders of nails comprise, for example onychomycosis, onychocryptosis, and onychodystrophy. Bacteria like staphylococci or yeast may cause the bacterial infection paronychia, a superficial infection of the nail wall.

The current treatment of onychomycosis generally falls into three categories:
a) systemic administration of antifungals,
b) surgical removal of all or part of the nail followed by topical treatment of the exposed tissue, or
c) topical application of conventional creams, lotions, gels or solutions on the infected nail, frequently including the use of bandages to keep these dosage forms in place on the nails.

Systemic, generally oral administration of an antifungal agent for the treatment of onychomycosis requires a long term treatment (6 months and longer) and the administration of high doses (200-400 mg per day) of an antifungal agent. Surgical removal of the whole nail or parts thereof is painful, requires bandaging of the whole toe or finger and causes undesirable cosmetic appearance. Topical dosage forms such as gels, creams, solutions, lotions, lacquers etc. have the drawback that the pharmaceutically active agent is not in sufficient intimate contact with the nail.

Plasters for the treatment of onychomycosis are known. For instance, WO-A-99/40955 discloses a pressure sensitive adhesive matrix patch for the treatment of onychomycosis. This device for treating fungal infections of toenails and fingernails is made up of an occlusive backing layer and a pressure-sensitive adhesive matrix layer wherein an effective amount of an antifungal agent is uniformly dispersed, optionally with a chemical enhancer. The matrix layer has a first surface adhering to the backing layer and a second surface adapted to be in diffusional contact with the infected nail and surrounding skin area.

A method for treating onychomycosis is described in U.S. Pat. No. 5,464,610. Within said method a plaster preparation is used comprising salicylic acid or a salt, ester or mixture thereof. Said plaster preparation is attached to a carries and the salicylic acid is present in the plaster preparation in an amount ranging from 10 to 80% by weight of the preparation.

Nail evulsion compositions and methods for evulsing nails and treating nail and nail bed infections are disclosed in U.S. Pat. No. 5,993,790. Claimed is a topical nail enamel composition comprising water-based nail lacquer, a preservative, urea, and a natural additive. Said nail enamel composition is suitable for the treatment of fungal, yeast, and bacterial infections of the nails and the nail beds.

U.S. Pat. No. 5,753,256 discloses a plaster for the treatment of nail mycoses which consists of a flexible covering film, a layer of an acrylate polymer matrix, inseparably linked to said covering film, and comprises an active compound selected form miconazole, econazole, isoconazole, tioconazole, terconazole, oxiconazole, ketoconazole, itraconazole, tolciclate, sulbentine, haloprogin, griseofulvin, cyclopirox, terbinafin, and salts of these compounds. The use of sertaconazole as antifungal agent is not mentioned.

It is object of the present invention to provide a plaster for prophylaxis and/or treatment of onychomycosis and of other dysfunctions or disorders of nails.

This object is solved by the plaster of the independent claims, the method of treatment claims, and the use of said plaster. Further advantageous features, aspects and details of the invention are evident from the dependent claims, the description, and the examples of the present application.

DESCRIPTION OF THE INVENTION

The present invention relates to a plaster which comprises at least one layer. Said layer is being designed to be in close contact with the nail and optionally with the surrounding skin. The layer comprises an adhesive, at least one skin and/or nail permeation enhancer, and a therapeutically effective amount of sertaconazole.

A preferred embodiment of said layer further comprises at least one additive selected from the group comprising further pharmaceutically active agents, binders, cross linkers, softeners, solvents, fillers, and/or antioxidants as described in detail below. Another preferred embodiment of the inventive plaster consists of at least two layers, one layer which comprises the adhesive, at least one skin and/or nail permeation enhancer, the therapeutically effective amount of sertaconazole, and optionally further additives selected from the group comprising further pharmaceutically active agents, binders, cross linkers, softeners, solvents, fillers, and/or antioxidants and a second layer, a backing layer, being designed to cover and protect the layer which is in close contact with the nail and optionally with the surrounding skin. Preferably, said backing layer is an occlusive backing layer.

The occlusive flexible backing layer holds and presses the plaster against the nail and skin in order to increase migration of sertaconazole from the layer into the nail, nail beds, and surrounding skin. Furthermore, the backing layer protects the layer form being contaminated. A preferred embodiment of said plaster comprises a colorless backing layer or a backing layer having an amber-like color. The plaster has sufficient flexibility in order to seal the affected nail exactly even if the nail has an uneven surface.

The backing layer is preferably made of polyethylene (such as LDPE, Plastotrans®), polypropylene, polyurethane, polyester (such as Revatrans®, TRICON GmbH, Freiburg), Guttagena® PVC NBR foil (such as Guttagena® WK 68, Kalle Pentaplast, Germany), cotton, cotton/viscose, silk, polyethyleneterephthalate (such as Hostaphan® RN 36 sil; Hostaphan® RN 100 sil, Loparex, Apeldoorn, The Netherlands), ethylene-methacrylic acid copolymers and/or mixtures of these materials. More preferably are siliconized polymers and/or copolymers.

As used herein, the term "layer" refers to a biocompatible adhesive containing sertaconazole and optionally further ingredients and/or additives with special biological functions suitable to allow and support migration and penetration of sertaconazole into the nails, nail beds, and the associated skin. In a preferred embodiment said layer is inseparably linked with the flexible occlusive backing layer.

A sufficiently large amount of sertaconazole and optionally further pharmaceutically active agents can be embedded into said adhesive which is preferably a gel-like or rubber-like adhesive in order to admit and maintain a continuing flow of the pharmaceutically active ingredient through the skin and nail for a longer time, preferably for one week.

The inventive plaster can be manufactured in any suitable shape, such as round, oval, rectangular or quadratic shape. Preferred plaster sizes are 0.5 cm$^2$, 0.85 cm$^2$, 1.5 cm$^2$, 2.3 cm$^2$, 2.5 cm$^2$, and 4.0 cm$^2$.

The dysfunction or disorder of nails comprises onychomycosis, onychocryptosis, nail psoriasis, melanonychia striata, white line disease, eczema, chronic onychia, discolored nails, thickened nails, and onychodystrophy. Said dysfunctions or disorders of nails are most likely caused or induced by fungi, yeasts, and/or bacteria. It is known that dermatophytes and yeasts are responsible for the majority of onychomycosis cases.

Onychomycosis, as a fungal infection, is regarded as a subgroup of onychodystrophy. Onychodystrophy comprises a number of nail dysfunctions and disorders such as onychocryptosis, melanonychia striata, white line disease, chronic paronychia, discolored nails, thickened nails, Unguis inflexus, coilonychia, scleronychia, onychogryphosis, onychauxis, onychoschisis, onychorrhexis, trachyonychia, cleaved and split nails.

The most prominent group of onychodystrophy apart from onychomycosis are induced by diseases of the skin such as neurodermitis (atopic eczema), and psoriasis. Furthermore, bacterial or viral infections are capable of causing or inducing onychodystrophy.

Also drugs such as antibiotics, anticoagulative agents, ACE inhibitors, betablockers, thiazides, cytostatic agents and the like are known to cause onychodystrophy. Another reason for onychodystrophy are systemic diseases such as avitaminoses, kidney failure, and heart failure. Another reason for onychodystrophy is the contact with chemical compounds such as acids, bases, oxidants and the like which cause burns, cauterizations, and also physical influences resulting in mechanical destruction of the nail plate. Finally, idiopathic causes exist for dysfunctions and/or disorders of the nail.

As used herein, the term "nail" refers to fingernails and toenails of mammals, especially humans.

A preferred embodiment of said plaster comprises a layer designed in that way that said layer seals the infected nail almost perfectly which results in an almost quantitative exclusion of air. In case of fungal nail infections caused by aerobic fungi the exclusion of air, that means more precisely the exclusion of atmospheric oxygen, increases the effectiveness of the inventive plaster. Depriving aerobic fungi of atmospheric oxygen can be achieved by forming an oxygen barrier over the exposed surface of the infected nail and the surrounding tissue. The oxygen barrier is formed by the layer which seals the infected nail and the surrounding tissue almost perfectly. Furthermore, the inventive plaster may optionally contain an additional oxygen scavenger. Suitable oxygen scavenger comprise transition metal chelates or complexes with, for instance salicylic acid and/or salicylate and/or polycarboxylic acids, or oxidizable organic acids or alcohols in combination with a catalyzing agent.

The layer of the inventive plaster contains sertaconazole in an effective amount of between 0.005-10 mg per cm$^2$ plaster, preferably 0.01-5 mg per cm$^2$ plaster, more preferably 0.5-4 mg, and most preferably 1.0-2.0 mg per cm$^2$ plaster.

It could be proven that in most cases sertaconazole shows higher efficacy against fungi such as *Trichophyton mentagrophytes, Trichophyton rubrum, Trichophyton interdigitale, T. schönleinii, T. verrucosum, T. violaceum, T. tonsurans, Trichophyton* spp., *M. canis, Candida albicans, C. guillermondii, C. krusei, C. parapsilosis, C. tropicalis, C. glabrata, Candida* spp., *Microsporum* spp., *Microsporum canis, Microsporum audonii, Microsporum gypseum, M. ferrugineum, Trichosporum beigelii, Trichosporum inkiin, Aspergillus niger, Alternaria, Acremonium, Fusarium,* and *Scopulariopsis* in comparison with other pharmaceutically active antifungal agents like econazole, ketonazole, miconazole, or bifonazole.

Preferred is the use of the inventive plasters for the prophylaxis and treatment of nail infections caused and/or mediated by *Candida albicans*.

The IUPAC name assigned to sertaconazole reads as follows:

(R,S)-1-[2-[(7-Chloro-3-benzo[b]thienyl)-methoxy]-2-(2,4-dichlorophenyl)-ethyl]-1H-imidazole or (R,S)-7-Chloro-3-[1-(2,4-dichlorophenyl)-2-(1H-imidazol-1-yl)-ethoxymethyl]-benzo[b]thiophene.

The Chemical Abstract Service (CAS) No. is 99592-32-2.

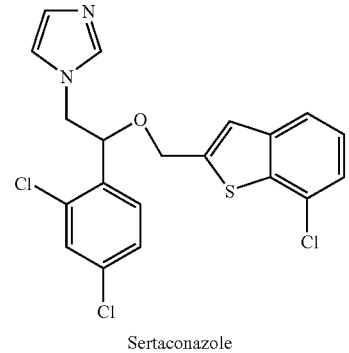

Sertaconazole

The compound sertaconazole is basic and forms pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, α-toluic acid, (o, m, p)-toluic acid, naphthylamine sulfonic acid, and other mineral or carboxylic acids as well as fatty acids and derivatives thereof well known to those skilled in the art. The salts are prepared by contacting the free base form with a sufficient amount of the desired acid to produce a salt in the conventional manner. Preferred as active ingredient is the mononitrate of sertaconazole or the free basic form itself.

The free base form may be regenerated by treating the salt with a suitable dilute aqueous base solution such as dilute aqueous sodium hydroxide, potassium carbonate, ammonia and sodium bicarbonate. The free base form differ from their corresponding salt form somewhat in certain physical properties, such as solubility in polar solvents, but the salts are otherwise equivalent to their corresponding free base form for purposes of this invention.

Suitable skin and/or nail permeation enhancer are well known to a person skilled in the art and may be selected from the group comprising of fatty acids, fatty acid esters, fatty acid amides, fatty alcohols, 2-(2-ethoxyethoxy)-ethanol, esters of glycerol, glycerol monolaurate, propylene glycol, polyethylene glycols, unsaturated polyglycolized glycerides (Labrafil M1944CS®, Gattefosse), saturated polyglycerides (Labrasol®, Gattefosse), a partial glyceride of ricinoleic acid (Softigen®, Hüls), Labrafac Hydro WL1219® (Gattefosse), Estasan® (Gattefosse), α-hydroxy acids, dimethylsulfoxide, decylmethylsulfoxide, pyrrolidones, salicylic acid, lactic acid, myristol, isopropyl myristate, dimethylformamide, dimethylacetamide, sodium dodecylsulfate, phospholipids, Transcutol® (Gattefosse), Eutanol® (Henkel), as well as mixtures comprising oleic acid/2-(2-ethoxyethoxy)-ethanol, oleic acid/Labrafil®, and oleic acid/Labrafac® (Gattefosse), preferably in a ratio of approximately 1:1, and the like. Also enzyme components, such as proteolytic enzymes which facilitate permeation of chemical substances through the hardened nail or keratin tissue, can be used as permeation enhancer.

Examples for most common fatty acids are capric-, lauric-, myristic-, palmitic-, margaric-, stearic-, arachidic-, behenic-, lignoceric-, myristoleic-, palmitoleic-, petroselinic-, oleic-, vaccenic-, gadoleic-, gondoic-, urucic-, nervonic-, linoleic-, γ-linolenic-, dihomo-γ-linolenic-, arachidonic-, 7,10,13,16-docosatetraenoic-, α-linolenic-, stearidonic-, 8,11,14,17-eicosatetraenoic-, 5,8,11,14,17-eicosapentaenoic-, 7,10,13,16,19-docosapentaenoic-, 4,7,10,13,16,19-docosahexaenoic-, 5,8,11-eicosatrienoic-, tariric-, santalbic-, stearolic-, 6,9-octadecenynoic-, pyrulic-, crepenynic-, heisteric-, t8,t10-octadecadiene-12-ynoic-, 5,8,11,14-eicosatetraynoic-, cerebronic-, hydroxynervonic-, brassylic-, and thapsic acid. Also useful are the lower alkyl ester and amides of said fatty acids or the corresponding alcohols thereof. The glycerol esters may also contain one or more of said fatty acids.

The skin and/or nail permeation enhancer supports and increases the penetration and permeation of sertaconazole through the skin and into the nails and nail beds. The term "penetration enhancement" or "permeation enhancement" relates to an increase in the permeability of a biological membrane or skin and nails. Skin and/or nail permeation enhancer are mostly used for increasing the rate at which a pharmaceutically active ingredient permeates through said membrane. The effect of permeation enhancement can be determined by the use of a diffusion cell apparatus as described by Merrit et al. (Diffusion Apparatus for Skin Penetration, J. Controlled Release, 1984, 1, 161-162) measuring the rate of diffusion of a pharmaceutically active agent, for instance sertaconazole, through animal or human skin.

An effective amount of a skin and/or nail permeation enhancer means an amount sufficient to provide the desired increase in membrane permeability and, accordingly, to obtain the desired depth of penetration and penetration of a sufficient amount of sertaconazole.

The inventive plaster preferably contains said skin and/or nail permeation enhancer in the layer in an amount of between 0.1% to 30% by weight of the adhesive, preferably 0.1% to 15% by weight of the adhesive, more preferably 0.5% to 10%, and most preferably 0.7% to 6% by weight of the layer.

Another preferred embodiment of the inventive plaster comprises further additives selected from the group comprising further pharmaceutically active agents, binders, cross linkers, softeners, solvents, fillers, and/or antioxidants.

Said additive or said additives, if present, are contained in the layer in an amount of between 2% to 80% by weight of the contact layer, preferably 5% to 40% by weight of the contact layer, more preferably between 8% to 30%, even more preferably between 12% to 25%, and most preferably in an amount between 15% to 20% by weight of the contact layer.

Binders characterize substances that bind or "glue" powders together and make them cohesive by forming the adhesive layer, thus serving as a further "adhesive" in the formulation. Suitable binders include non-natural sugars, natural sugars such as sucrose, starches derived from wheat, corn rice and potato; synthetic and natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate, polyethylene glycol and waxes.

If present, the amount of binder in the adhesive can range from about 1 to 50% by weight of the adhesive, preferably from about 10 to about 50% by weight of the adhesive, more preferably from about 20 to about 50% by weight, even more preferably from about 30 to about 40% by weight.

Cross linkers may be selected from the group comprising cross linking agents such as aluminum acetylacetonate, acrylate-vinylacetate copolymer, aluminum acetonate, titanium acetylacetonate, titanium acetonate, and succinic acid.

If present, the amount of cross linkers in the adhesive can range from about 0.01 to 30% by weight of the adhesive, preferably from about 0.1 to about 50% by weight of the adhesive, more preferably from about 10 to about 50% by weight, even more preferably from about 30 to about 40% by weight.

Softener may be chosen from the group comprising dibutylsebacate (DBS), Macrogol® (Clariant, Frankfurt, Germany) and the like.

If present, the amount of softener in the adhesive can range from about 0.001 to 25% by weight of the adhesive, preferably from about 0.01 to about 10% by weight of the adhesive, more preferably from about 0.1 to about 6% by weight, even more preferably from about 0.5 to about 3% by weight.

Suitable solvents for the inventive plaster may be selected form purified water; ketones such as acetone, butanone, 2-pentanone, 3-pentanone; alcohols such as ethanol, propanol, isopropanol, butanol, isobutanol, sec.-butanol, tert.-butanol; esters such as acetic acid ethyl ester, acetic acid propyl ester and the like. Furthermore, mixtures of said solvents can also be used. Suitable co-solvents may be used together with the above-mentioned solvents or mixtures of solvents, said co-solvents may be selected from the group comprising lactic acid, salicylic acid, succinic acid, urea, Miglyol® 812 (Chemische Werke Hüls, Marl, Germany), triglycerides, ethyloleate, glycerylmonododecanoate, olein, oleate, Macrogol® 6000, and lecithin.

If present, the amount of solvents or the total amount of solvents and co-solvents in the adhesive can range from about 0.5 to 70% by weight of the adhesive, preferably from about 3 to about 60% by weight of the adhesive, more preferably from about 10 to about 50% by weight, even more preferably from about 20 to about 40% by weight, and most preferably from about 10 to about 30% by weight of the adhesive.

Fillers may be chosen from the group comprising silica, silicic acid, preferably colloidal silica and colloidal silicic acid, lactose, Aerosil® such as Aerosil® 200 (Degussa-Hüls, Frankfurt, Germany), starch, Bentonit® (Südchemie, Mannheim, Germany) and the like.

If present, the amount of fillers in the adhesive can range from about 0.01 to 15% by weight of the adhesive, preferably from about 0.1 to about 10% by weight of the adhesive, more preferably from about 0.3 to about 6% by weight, even more preferably from about 0.5 to about 3% by weight.

Butylhydroxytoluene (BHT) may be mentioned as an example for a suitable antioxidant. Antioxidants are well known to a person skilled in the art and may be selected form the antioxidants of the state of the art.

If present, the amount of antioxidants in the adhesive can range from about 0.001 to 10% by weight of the adhesive, preferably from about 0.005 to about 6% by weight of the adhesive, more preferably from about 0.01 to about 3% by weight, even more preferably from about 0.05 to about 1% by weight.

The inventive plaster may optionally contain a pharmaceutically active amount of an additional antifungal agent, such as fluconazole (Diflucan®), butoconazole, enilconazole, fenticonazole, sulconazole, naftifidine, clioquinol, iodoquinol, rimoprogin, griseofulvin, terbinafine (Lamisil®, Novartis Pharma), clotrimazole, itraconazole (Sempera®, Janssen Pharmaceutical), tioconazole, miconazole, tolnaftate, pyrogallol, econazole, isoconazole, terconazole, oxiconazole, voriconazole, amphotericin B, nystatin, tolciclate, sulbentine, ketoconazole, ciclopirox (Batrafen®, Aventis Pharma), amorolfine, bifonazole, sodium pyrithione, salicylic acid and/or salts of these antifungal agents.

These further pharmaceutically active agents can roughly by divided into five groups comprising polyenes such as amphotericin B and nystatin; azoles especially imidazoles such as miconazole and sertaconazole; triazoles such as itraconazole, fluconazole, and voriconazole; allylamines such as naftifidine and terbinafine; morpholines such as amorolfine; and benzofuranes such as griseofulvin.

If present, said additional pharmaceutically active agent is contained in the layer in an amount of between 0.005-10 mg per cm$^2$ plaster, preferably in an amount of 0.01-5.0 mg, more preferably in an amount of 0.5-2.0 mg, and most preferably in an amount of 1.3-1.5 mg per cm$^2$ plaster.

Suitable adhesives for the inventive plaster may comprise acrylic copolymers, also known as "acrylic adhesives", like National Starch Durotak® 80-1196, National Starch Durotak® 387-2825, or Monsanto Gelva 737; polyacrylamide; rubber-based adhesives, also called "rubber adhesives", such as polyisobutylene (PIB) (e.g. Adhesive Research MA-24), polyisoprene, styrene-isoprene copolymers, or urethane rubbers; and silicone based adhesives, so called "silicone adhesives", such as Dow Bio-PSA.

The adhesives that may be used according to the invention represent a polymer, preferably an acrylate copolymer. Suitable monomers or mixtures of monomers for the manufacture of said acrylate polymer comprise methyl acrylate, methyl methacrylate, butyl acrylate, butyl methacrylate, isooctyl acrylate, isooctyl methacrylate, aminoalkyl acrylate, aminoalkyl methacrylate, aminoalkyl methacrylate copolymers (such as EUDRAGIT® E 100, EUDRAGIT® RL, EUDRAGIT® RS, EUDRAGIT® NE 30 D commercially available from Röhm, Degussa-Hüls Group), hydroxyethyl acrylate, hydroxyethyl methacrylate, 2-ethylhexyl acrylate, 2-ethylhexyl methacrylate, acrylic acid, methacrylic acid, vinyl acetate, and glycidyl methacrylate. Acrylate-based adhesives are commercially available from National Starch Chemical B. V., Zutphen, NL, under the name Durotak®. Examples of said product class are Durotak® 280-2287 (51% solution or solid matter), Durotak® 326-1753 (37% solution or solid matter), Durotak® 280-1753 (33% solution or solid matter), Durotak® 901-1052 (48% solution or solid matter), Durotak® 80-1196 (solid matter), and Durotak® 387-2825 (50% solution).

The adhesive is contained in the plaster of the present invention in an amount of between 40% to 95% by weight of the plaster, preferably between 60 to 90%, more preferably between 70% to 90%, and most preferably between 80% to 90% by weight of the plaster.

The present invention discloses a combination therapy wherein the plaster is used in combination with a systemic treatment of onychomycosis or other systemic treatments for dysfunctions or disorders of nails or nail growth.

Said combination therapy is especially useful for prophylaxis and/or treatment of onychomycosis, onychocryptosis, nail psoriasis, melanonychia striata, white line disease, eczema, chronic onychia, discolored nails, thickened nails, and onychodystrophy.

As used herein, the term "plaster" refers to any device which can be applied to the nail and which comprises a sertaconazole containing layer which is pressed against the nail surface. Suitable plaster devices include plasters or preformed films based upon rubbers, acrylics, urethanes, silicone materials, polyvinylalkylethers, gels, and impregnated microporous membranes. Said plaster device could also be combined with or incorporated or formed into shape of an artificial or fake nail in order to improve cosmetic appearance.

Furthermore, the present invention describes the use of the plaster for prophylaxis and/or treatment of a dysfunction or disorder of nails comprising a layer being designed to be in close contact with the nail and optionally with the surrounding skin wherein said layer comprises a) an adhesive;

b) at least one skin and/or nail permeation enhancer; and c) a therapeutically effective amount of sertaconazole.

Preferred is the use of a plaster comprising further additives selected from the group comprising further pharmaceutically active agents, binders, cross linkers, softeners, solvents, fillers, and/or antioxidants as described above in detail. Also preferred is the use of plasters having a second layer designed as a backing layer. Most preferably is an embodiment wherein the second layer is an occlusive backing layer.

The inventive plaster is preferably used for the transdermal and/or transnail prophylaxis and/or treatment of a dysfunction or disorder of nails by adhesively securing to the nail and optionally the surrounding skin of said nail the plaster. Said plaster consists of a layer comprising an adhesive, at least one skin and/or nail permeation enhancer, and a therapeutically effective amount of sertaconazole and said layer being designed to be in close contact with the nail and optionally with the surrounding skin. Optionally said plaster may further comprise a backing layer, preferably an occlusive backing layer.

Especially, the inventive plaster is highly useful for the prevention and/or treatment of onychomycosis, onychocryptosis, nail psoriasis, melanonychia striata, white line disease, eczema, chronic onychia, discolored nails, thickened nails, and onychodystrophy.

Most likely, said dysfunctions or disorders of nails is induced or caused by fungal, yeast, or bacterial infection of the nails and/or the nail beds or by skin diseases, drugs, physical influences, systemic diseases, contact with chemicals, or idiopathic causes.

Combination therapy disclosed herein can be applied by dysfunction or disorder of nails is induced or caused by fungal, yeast, or bacterial infection of the nails and/or the nail beds, or in the context of skin diseases, such as neurodermitis (atopic eczema), psoriasis and the like, or caused by drugs such as antibiotics, anticoagulative agents, ACE inhibitors, betablockers, thiazides, cytostatic agents, or caused by systemic diseases such as avitaminoses, kidney failure, and heart failure, or caused by chemical compounds such as acids, bases, oxidants and the like, or caused by physical influences resulting in mechanical destruction of the nail plate.

One important aspect of the present invention is that the use of the plaster does not require the procedure of drilling at least one hole into the nail and/or daily scraping of the nail. Another advantage of the present invention is that the plaster is easy to use, convenient and user-friendly.

Furthermore, the inventive plaster can be used in combination with a systemic treatment of a dysfunction or disorder of nails, such as onychomycosis, onychocryptosis, nail psoriasis, melanonychia striata, white line disease, eczema, chronic onychia, discolored nails, thickened nails, and onychodystrophy.

Melanonychia striata or longitudinal melanonychia refers to any linear tan, brown, or black pigmentation within the nail plate that results from increased melanin deposition. Onychomycosis is a fungal infection of the nail caused by dermatophytes, yeasts, or non-dermatophyte moulds. It is the most common nail disorder.

Another aspect of the present invention is directed to a method for prophylaxis and/or treatment of a dysfunction or disorder of nails by securing to the nail and optionally the surrounding skin of said nail a plaster comprising a layer which comprises:

a) an adhesive;
b) at least one skin and/or nail permeation enhancer; and
c) a therapeutically effective amount of sertaconazole.

Within said method preferably a plaster is used wherein said layer further comprises at least one additive selected from the group comprising further pharmaceutically active agents, binders, cross linkers, softeners, solvents, fillers, and/or antioxidants as described above in detail. Also preferred is the presence of an additional layer, a so called backing layer, and more preferably an occlusive backing layer.

The present invention discloses a method for the transdermal and/or transnail delivery of a sufficient amount of sertaconazole to an affected nail, nail bed and surrounding tissue by adhesively securing to the nail and optionally the surrounding skin the plaster, in order to treat a dysfunction or disorder of growth of said nail. Especially, said finger- and/or toenails are affected by onychomycosis, onychocryptosis, nail psoriasis, melanonychia striata, white line disease, eczema, chronic onychia, discolored nails, thickened nails, and onychodystrophy.

One advantage of said inventive method is exhibited by the fact that this method does not require drilling holes into the nails and/or daily scraping of the nails.

The inventive method can also be applied in combination with a systemic treatment of a dysfunction or disorder of nails. Especially, a combination of the inventive method with a systemic treatment has been proven effective for the dysfunctions or disorders of nails comprising onychomycosis, onychocryptosis, nail psoriasis, melanonychia striata, white line disease, eczema, chronic onychia, discolored nails, thickened nails, and onychodystrophy.

EXAMPLES

The following examples shall exemplify the present invention and shall not limit the scope of the present invention to these specific embodiments.

The plasters or nail patches may preferably comprise a backing layer and/or a release liner. The backing layer, if present, is preferably made from PVC such as Guttagena PVC NBR foil and the release liner is preferably made of PET such as PET foil with both sides siliconized (100 μm).

Example 1

Plaster 1

Compounds of the Contacting Layer for 1.0 cm² Plaster

| No. | Compound | Concentration |
| --- | --- | --- |
| 1 | sertaconazole | 1.65 mg |
| 2 | durotak 387-2825 | 8.80 mg |
| 3 | lactic acid | 0.11 mg |
| 4 | aerosil 200 | 0.33 mg |
| 5 | aluminum acetylacetonate | 0.11 mg |

Results:

Double, randomized, multicentric clinical trails were conducted on 23 patients suffering from fungal infection of fingernails After a treatment period of six month with a subsequent observation period of one month, 70.6% of the patients treated with the inventive plaster showed a decrease in severity of the fungal infection and a negative result of mycological culture after 24 weeks of treatment.

Only 5.3% of the treated patients showed minor side effects during the treatment period. Said side effects were characterized as skin scaling of the tissue surrounding the infected nail.

One advantageous effect of the plasters disclosed herein is that the plaster has only to be replaced once a week and not, for instance, daily. Therefore, an excess of sertaconazole is used in order to ensure that a sufficient amount of the antimycotic agent sertaconazole will after one week still be present in the adhesive layer of the plaster. The remaining amount of sertaconazole in the plaster has a prophylactic effect and prevents the development of secondary mycoses and diminishes the risk of third persons to be infected by the patient.

The plasters 2-6 according to examples 2-6 give similar results while the plaster according to the formulation of example 1 is most preferred.

The treatment period can last in isolated cases one year or longer. Normally, the treatment period will be one to several months under the condition that the plaster is replaced weekly.

Example 2

Plaster 2

Composition for the Manufacture of 1 cm² Plaster

| No. | Compound | Amount |
| --- | --- | --- |
| 1 | sertaconazole | 1-2 mg |
| 2 | Durotak 87-2852 solution (36.1%) | 22.2 mg |
| 3 | Ethyl alcohol (96%) | 2 mg |

The compound will be weighed and stirred until homogeneity. The mixture will be applied to a siliconized polyester sheet (thickness 75 μm, from Loparex, Apeldorn, NL). The wet thickness of the glue film amounts 400 μm. Following 15 minutes drying at 60° C. in drying cabinet and storage at 25°

C. for 12 hours the glue layer will be covered with polyolefine film of 50 μm thickness (Cotran No. 9722, from 3M-Medica, Borken, Germany).

Finally the self-adhesive plaster in the size of finger or toe nails will be punched from the sheet.

Example 3

Plaster 3

Composition for the Manufacture of 1 cm² Plaster

| No. | Compound | Amount |
|---|---|---|
| 1 | sertaconazole | 1.8 mg |
| 2 | Durotak 36-6172 solution (57.1%) | 14 mg |
| 3 | n-Heptan | 2 mg |

The compound will be weighed and stirred until homogeneity. The mixture will be applied to a siliconized polyester sheet (thickness 75 μm, from Loparex, Apeldorn, NL). The wet thickness of the glue film amounts 400 μm. Following 15 minutes drying at 60° C. in drying cabinet and storage at 25° C. for 12 hours the glue layer will be covered with polyolefine film of 50 μm thickness (Cotran No. 9722, from 3M-Medica, Borken, Germany).

Finally the self-adhesive plaster in the size of finger or toe nails will be punched from the sheet.

Example 4

Plaster 4

Composition for the Manufacture of 1 cm² Plaster

| No. | Compound | Amount |
|---|---|---|
| 1 | sertaconazole | 1.5 mg |
| 2 | Durotak 87-2100 (52.9%) | 15.1 mg |
| 3 | Ethyl alcohol (96%) | 3 mg |

The compound will be weighed and stirred until homogeneity. The mixture will be applied to a siliconized polyester sheet (thickness 75 μm, from Loparex, Apeldorn, NL). The wet thickness of the glue film amounts 400 μm. Following 15 minutes drying at 70° C. in drying cabinet and storage at 25° C. for 12 hours the glue layer will be covered with polyolefine film of 50 μm thickness (Cotran No. 9722, from 3M-Medica, Borken, Germany).

Finally the self-adhesive plaster in the size of finger or toe nails will be punched from the sheet.

Example 5

Plaster 5

Composition for the Manufacture of 1 cm² Plaster

| No. | Compound | Amount |
|---|---|---|
| 1 | sertaconazole | 1.7 mg |
| 2 | Durotak 387-2516 solution (42.5%) | 18.8 mg |
| 3 | Ethyl alcohol (96%) | 3 mg |

The compound will be weighed and stirred until homogeneity. The mixture will be applied to a siliconized polyester sheet (thickness 75 μm, from Loparex, Apeldorn, NL). The wet thickness of the glue film amounts 400 μm. Following 15 minutes drying at 60° C. and 10 minutes at 80° C. in drying cabinet and storage after cooling the glue layer will be covered with polyolefine film of 50 μm thickness (Cotran No. 9722, from 3M-Medica, Borken, Germany).

Finally the self-adhesive plaster in the size of finger or toe nails will be punched from the sheet.

Example 6

Plaster 6

Compounds of the Contacting Layer for 1.0 cm² Plaster

| No. | Compound | Concentration |
|---|---|---|
| 1 | EUDRAGIT ® E 100 | 42.2 g |
| 2 | sertaconazole | 17.7 g |
| 3 | dibutylsebacate | 19.0 g |
| 4 | succinic acid | 3.8 g |
| 5 | acetone | 21.0 g |
| 6 | isopropanol | 2.3 g |
| 7 | ethanol | 11.7 g |

Equipment:

The solution is prepared in a high-speed stirred tank. The stirrer may be a dissolver disc, for example, which guarantees thorough mixing also at rising viscosity. On a laboratory scale, coating and drying are performed in a laboratory coating unit with integrated dryer (LTSV/LTF by W. Mathis AG, Switzerland).

Instructions for Processing:

Acetone, isopropanol, and ethanol is placed in a stirred tank and EUDRAGIT® E 100 is added in portions over a period of 90 minutes. The stirrer is set to a speed which excludes sediment formation while dissolving EUDRAGIT® E 100. Dibutylsebacate is added swiftly and stirring is continued for another 20 minutes. Thereafter sertaconazole is added and succinic acid is given to the polymer solution in portions with intensive stirring. After complete addition of succinic acid the polymer solution is stirred for additional 20 minutes.

Coating is performed with the final polymer solution at the following parameters:

Coating: approximately 100 g of said polymer solution is applied to the backing layer foil (15 μm thickness, Revatrans® MN, Tricon GmbH Freiburg) by means of a rotary doctor blade at a nip of 200 μm.

Drying: Drying is performed at 60° C. for 10 minutes, circulating air: 1500 m³/h, exhaust air: 80 m³/h.

The invention claimed is:

1. Plaster comprising:
a layer being designed to be in close contact with the nail and optionally with the surrounding skin;
said layer comprising:
a) an adhesive;
b) at least one skin and/or nail permeation enhancer; and
c) a therapeutically effective amount of a free base of sertaconazole.

2. Plaster according to claim 1 wherein said layer further comprises at least one additive selected from the group comprising further pharmaceutically active agents, binders, cross linkers, softeners, solvents, fillers, and/or antioxidants.

3. Plaster according to claim 1 further comprising a backing layer.

4. Plaster according to claim 3 wherein said backing layer is an occlusive backing layer.

5. Plaster according to claim 1 wherein sertaconazole is contained in the adhesive in an amount of between 0.01-5 mg per $cm^2$ plaster.

6. Plaster according to claim 1 wherein the skin and/or nail permeation enhancer is selected from the group comprising fatty acids, fatty acid esters, fatty acid amides, fatty alcohols, 2-(2-ethoxyethoxy)-ethanol, esters of glycerol, glycerol monolaurate, propylene glycol, polyethylene glycols, unsaturated polyglycolized glycerides, saturated polyglycerides, a partial glyceride of ricinoleic acid, α-hydroxy acids, dimethylsulfoxide, decylmethylsulfoxide, pyrrolidones, salicylic acid, lactic acid, myristol, isopropyl myristate, dimethylformamide, dimethylacetamide, sodium dodecylsulfate, phospholipids, and proteolytic enzymes.

7. Plaster according to claim 1 wherein the skin and/or nail permeation enhancer is contained in the layer in an amount of between 0.7% to 6% by weight of the layer.

8. Plaster according to claim 1 wherein the adhesive is selected from the group comprising acrylic adhesives, rubber adhesives, and/or silicone adhesives.

9. Plaster according to claim 1 wherein the adhesive is contained in the plaster in an amount of between 80% to 90% by weight of the layer.

10. Plaster according to claim 2 wherein the additives are contained in the layer in an amount of between 15% to 20% by weight of the layer.

11. Plaster according to claim 2 wherein the further pharmaceutically active agent is selected from the group fluconazole, butoconazole, enilconazole, fenticonazole, sulconazole, naftifidine, clioquinol, iodoquinol, rimoprogin, griseofulvin, terbinafine, clotrimazole, itraconazole, tioconazole, miconazole, tolnaftate, pyrogallol, econazole, isoconazole, terconazole, oxiconazole, voriconazole, amphotericin B, nystatin, tolciclate, sulbentine, ketoconazole, ciclopirox, amorolfine, bifonazole, sodium pyrithione, salicylic acid and/or salts of these pharmaceutically active agents.

12. Plaster according to claim 2 wherein the further pharmaceutically active agent is contained in the layer in an amount of between 0.01-5 mg per $cm^2$ plaster.

13. Process of using a plaster by adhesively securing to a nail a plaster comprising a layer being designed to be in close contact with the nail and optionally with the surrounding skin;
said layer comprising:
a) an adhesive;
b) at least one skin and/or nail permeation enhancer; and
c) a therapeutically effective amount of a free base of sertaconazole for prophylaxis and/or treatment of a dysfunction or disorder of nails.

14. Process of using according to claim 13 wherein said layer further comprises at least one additive selected from the group comprising further pharmaceutically active agents, binders, cross linkers, softeners, solvents, fillers, and/or antioxidants.

15. Process of using according to claim 13 wherein said plaster further comprises a backing layer.

16. Process of using according to claim 15 wherein said backing layer is an occlusive backing layer.

17. Process of using according to claim 13 for the transdermal and/or transnail prophylaxis and/or treatment of a dysfunction or disorder of nails by adhesively securing to the nail and optionally the surrounding skin of said nail the plaster comprising a layer being designed to be in close contact with the nail and optionally with the surrounding skin;
said layer comprising:
a) an adhesive;
b) at least one skin and/or nail permeation enhancer; and
c) a therapeutically effective amount of sertaconazole.

18. Process of using according to claim 13 wherein the dysfunction or disorder of nails comprises onychomycosis, onychocryptosis, nail psoriasis, melanonychia striata, white line disease, eczema, chronic onychia, discolored nails, thickened nails, and onychodystrophy.

19. Process of using according to claim 13 wherein said dysfunction or disorder of nails is induced or caused by drugs, systemic diseases, chemical compounds, physical influences, fungal, yeast, or bacterial infection of the nails and/or the nail beds, or in the context of skin diseases.

20. Process of using according to claim 13 wherein sertaconazole is contained in the adhesive in an amount of between 0.01-5 mg per $cm^2$ plaster.

21. Process of using according to claim 13 wherein the skin and/or nail permeation enhancer is selected from the group comprising fatty acids, fatty acid esters, fatty acid amides, fatty alcohols, 2-(2-ethoxyethoxy)-ethanol, esters of glycerol, glycerol monolaurate, propylene glycol, polyethylene glycols, unsaturated polyglycolized glycerides, saturated polyglycerides, a partial glyceride of ricinoleic acid, α-hydroxy acids, dimethylsulfoxide, decylmethylsulfoxide, pyrrolidones, salicylic acid, lactic acid, myristol, isopropyl myristate, dimethylformamide, dimethylacetamide, sodium dodecylsulfate, phospholipids, and proteolytic enzymes.

22. Process of using according to claim 13 wherein the skin and/or nail permeation enhancer is contained in the layer in an amount of between 0.7% to 6% by weight of the layer.

23. Process of using according to claim 13 wherein the adhesive is selected from the group comprising acrylic adhesives, rubber adhesives, and/or silicone adhesives.

24. Process of using according to claim 13 wherein the adhesive is contained in the plaster in an amount of between 80% to 90% by weight of the layer.

25. Process of using according to claim 13 wherein the additives are contained in the layer in an amount of between 15% to 20% by weight of the layer.

26. Process of using according to claim 13 wherein the further pharmaceutically active agent is selected from the group comprising fluconazole, butoconazole, enilconazole, fenticonazole, sulconazole, naftifidine, clioquinol, iodoquinol, rimoprogin, griseofulvin, terbinafine, clotrimazole, itraconazole, tioconazole, miconazole, tolnaftate, pyrogallol, econazole, isoconazole, terconazole, oxiconazole, voriconazole, amphotericin B, nystatin, tolciclate, sulbentine, ketoconazole, ciclopirox, amorolfine, bifonazole, sodium pyrithione, salicylic acid and/or salts of these pharmaceutically active agents.

27. Process of using according to claim 13 wherein the further pharmaceutically active agent is contained in the layer in an amount of between 0.01-5 mg per $cm^2$ plaster.

28. Process of using according to claim 13 wherein said use does not require drilling a hole into the nails and/or daily scraping of the nail.

29. Process of using according to claim 13 in combination with a systemic treatment of a dysfunction or disorder of nails, especially of onychomycosis or other forms of onychodystrophy.

30. Process of using according to claim 29 wherein the dysfunction or disorder of nails comprises onychomycosis, onychocryptosis, nail psoriasis, melanonychia striata, white line disease, eczema, chronic onychia, discolored nails, thickened nails, and onychodystrophy.

31. Combination therapy wherein the plaster comprises a layer being designed to be in close contact with the nail and optionally with the surrounding skin; said layer comprising: a) an adhesive; b) at least one skin and/or nail permeation enhancer; and c) a therapeutically effective amount of a free base of sertaconazole is used in combination with a systemic treatment of a dysfunction or disorder of nails, especially of onychomycosis or other forms of onychodystrophy.

32. Combination therapy according to claim 31 wherein the dysfunction or disorder of nails comprises onychomycosis, onychocryptosis, nail psoriasis, melanonychia striata, white line disease, eczema, chronic onychia, discolored nails, thickened nails, and onychodystrophy.

33. Combination therapy according to claim 31 wherein said dysfunction or disorder of nails is induced or caused by drugs, systemic diseases, chemical compounds, physical influences, fungal, yeast, or bacterial infection of the nails and/or the nail beds, or in the context of skin diseases.

34. Method for prophylaxis and/or treatment of a dysfunction or disorder of nails by securing to the nail and optionally the surrounding skin of said nail a plaster comprising a layer, said layer comprising
   a) an adhesive;
   b) at least one skin and/or nail permeation enhancer; and
   c) a therapeutically effective amount of a free base of sertaconazole.

35. Method according to claim 34 wherein said layer further comprises at least one additive selected from the group comprising further pharmaceutically active agents, binders, cross linkers, softeners, solvents, fillers, and/or antioxidants.

36. Method according to claim 34 wherein said plaster further comprises a backing layer.

37. Method according to claim 34 wherein said backing layer is an occlusive backing layer.

38. Method according to claim 34 for the transdermal and/or transnail prophylaxis and/or treatment of a dysfunction or disorder of nails by adhesively securing to the nail and optionally the surrounding skin of said nail the plaster comprising a layer being designed to be in close contact with the nail and optionally with the surrounding skin;
   said layer comprising:
   a) an adhesive;
   b) at least one skin and/or nail permeation enhancer; and
   c) a therapeutically effective amount of a free base of sertaconazole.

39. Method according to claim 34 wherein the dysfunction or disorder of nails comprises onychomycosis, onychocryptosis, nail psoriasis, melanonychia striata, white line disease, eczema, chronic onychia, discolored nails, thickened nails, and onychodystrophy.

40. Method according to claim 34 wherein said dysfunction or disorder of nails is induced or caused by drugs, systemic diseases, chemical compounds, physical influences, fungal, yeast, or bacterial infection of the nails and/or the nail beds, or in the context of skin diseases.

41. Method according to claim 34 wherein sertaconazole is contained in the adhesive in an amount of between 0.01-5 mg per cm$^2$ plaster.

42. Method according to claim 34 wherein the skin and/or nail permeation enhancer is selected from the group comprising fatty acids, fatty acid esters, fatty acid amides, fatty alcohols, 2-(2-ethoxyethoxy)-ethanol, esters of glycerol, glycerol monolaurate, propylene glycol, polyethylene glycols, unsaturated polyglycdized glycerides, saturated polyglycerides, a partial glyceride of ricinoleic acid, α-hydroxy acids, dimethylsulfoxide, decylmethylsulfoxide, pyrrolidones, salicylic acid, lactic acid, myristol, isopropyl myristate, dimethylformamide, dimethylacetamide, sodium dodecylsulfate, phospholipids, and proteolytic enzymes.

43. Method according to claim 34 wherein the skin and/or nail permeation enhancer is contained in the layer in an amount of between 0.7% to 6% by weight of the layer.

44. Method according to claim 34 wherein the adhesive is selected from the group comprising acrylic adhesives, rubber adhesives, and silicone adhesives.

45. Method according to claim 34 wherein the adhesive is contained in the plaster in an amount of between 80% to 90% by weight of the layer.

46. Method according to claim 34 wherein the additives are contained in the layer in an amount of between 15% to 20% by weight of the layer.

47. Method according to claim 34 wherein the further pharmaceutically active agent is selected from the group comprising fluconazole, butoconazole, enilconazole, fenticonazole, sulconazole, naftifidine, clioquinol, iodoquinol, rimoprogin, griseofulvin, terbinafine, clotrimazole, itraconazole, tioconazole, miconazole, tolnaftate, pyrogallol, econazole, isoconazole, terconazole, oxiconazole, voriconazole, amphotericin B, nystatin, tolciclate, sulbentine, ketoconazole, ciclopirox, amorolfine, bifonazole, sodium pyrithione, salicylic acid and/or salts of these pharmaceutically active agents.

48. Method according to claim 34 wherein the further pharmaceutically active agent is contained in the layer in an amount of between 0.01-5 mg per cm$^2$ plaster.

49. Method according to claim 34 wherein said method does not require drilling a hole into the nails and/or daily scraping of the nail.

50. Method according to claim 34 in combination with a systemic treatment of a dysfunction or disorder of nails, especially of onychomycosis or other forms of onychodystrophy.

51. Method according to claim 50 wherein the dysfunction or disorder of nails comprises onychomycosis, onychocryptosis, nail psoriasis, melanonychia striata, white line disease, eczema, chronic onychia, discolored nails, thickened nails, and onychodystrophy.

52. Method according to claim 50 wherein said dysfunction or disorder of nails is induced or caused by drugs, systemic diseases, chemical compounds, physical influences, fungal, yeast, or bacterial infection of the nails and/or the nail beds, or in the context of skin diseases.

* * * * *